US012594440B2

(12) United States Patent
Sun et al.

(10) Patent No.: US 12,594,440 B2
(45) Date of Patent: Apr. 7, 2026

(54) METHODS OF TREATMENT FOR ANOREXIA NERVOSA

(71) Applicant: SHANGHAI HAOYISHENG ENTERPRISE MANAGEMENT PARTNERSHIP (LIMITED PARTNERSHIP), Shanghai (CN)

(72) Inventors: Bomin Sun, Shanghai (CN); Halimureti Paerhati, Shanghai (CN); Shikun Zhan, Shanghai (CN); Dianyou Li, Shanghai (CN); Wei Liu, Shanghai (CN)

(73) Assignee: SHANGHAI HAOYISHENG ENTERPRISE MANAGEMENT PARTNERSHIP (LIMITED PARTNERSHIP), Shanghai (CN)

( * ) Notice: Subject to any disclaimer, the term of this patent is extended or adjusted under 35 U.S.C. 154(b) by 1 day.

(21) Appl. No.: 18/764,332

(22) Filed: Jul. 4, 2024

(65) Prior Publication Data

US 2026/0007907 A1 Jan. 8, 2026

(51) Int. Cl.
*A61N 7/02* (2006.01)

(52) U.S. Cl.
CPC .......... *A61N 7/02* (2013.01); *A61N 2007/027* (2013.01)

(58) Field of Classification Search
None
See application file for complete search history.

(56) References Cited

U.S. PATENT DOCUMENTS

| | | |
|---|---|---|
| 2014/0357932 A1 | 12/2014 | Lozano |
| 2020/0315829 A1 | 10/2020 | Schlesinger et al. |
| 2025/0041577 A1* | 2/2025 | Shapira .............. A61K 41/0033 |

OTHER PUBLICATIONS

Davidson et al., "Magnetic Resonance-Guided Focused Ultrasound Capsulotomy for Treatment-Resistant Psychiatric Disorders," Jul. 30, 2020, Operative Neurosurgery 19(6):p. 741-749. (Year: 2020).*
Liu et al., "Long-Term Follow-up Study of MRI-Guided Bilateral Anterior Capsulotomy in Patients With Refractory Anorexia Nervosa," Jul. 2018, Neurosurgery 83(1):p. 86-92. (Year: 2018).*
Davidson et al., "Technical and radiographic considerations for magnetic resonance imaging-guided focused ultrasound capsulotomy", Sep. 25, 2020, J Neurosurg 135:291-299, 2021. (Year: 2020).*
Jung et al., "Bilateral thermal capsulotomy with MR-guided focused ultrasound for patients with treatment-refractory obsessive-compulsive disorder: a proof-of-concept study," Nov. 25, 2014, Molecular Psychiatry (2015) 20, 1205-1211. (Year: 2014).*

(Continued)

*Primary Examiner* — Keith M Raymond
*Assistant Examiner* — Ashish S. Jasani
(74) *Attorney, Agent, or Firm* — SZDC Law PC

(57) ABSTRACT

A method is provided for treating neurogenic anorexia nervosa in a subject in need thereof, using a magnetic resonance guided focused ultrasound treatment system. The method comprises applying high-intensity focused ultrasound energy to multiple treatment target points on the bilateral anterior limbs of the left and right internal capsules of the subject to regulate the bilateral anterior limbs of the subject; and inducing normalization of weight in the subject.

18 Claims, 4 Drawing Sheets

(56) References Cited

OTHER PUBLICATIONS

Germann et al., "Potential optimization of focused ultrasound capsulotomy for obsessive compulsive disorder," Jun. 19, 2021, Brain 2021: 144; 3529-3540) (Year: 2021).*

Kim et al. , "A study of novel bilateral thermal capsulotomy with focused ultrasound for treatment-refractory obsessive-compulsive disorder: 2-year follow-up," (May 2, 2018), J Psychiatry Neurosci 2018;43(5). (Year: 2018).*

Davidson et al., "Magnetic resonance-guided focused ultrasound capsulotomy for refractory obsessive compulsive disorder and major depressive disorder: clinical and imaging results from two phase I trials," (May 14, 2020), Molecular Psychiatry (2020) 25:1946-1957. (Year: 2020).*

Jason M. Nagata et al., "Comparisons of bone density and body composition among adolescents with anorexia nervosa and atypical anorexia nervosa" Int J Eat Disord. 2019; 1-6.

Adam Wysokiński et al., "Mechanisms of the anorexia of aging—a review" AGE (2015) 37:81 (Aug. 1, 2015).

Michael M. H. Yang et al., "Development and validation of a clinical prediction score for poor postoperative pain control following elective spine surgery" J Neurosurg Spine Sep. 15, 2020, pp. 1-10 (Sep. 15, 2020).

Marwan El Ghoch et al., "Anorexia Nervosa and Body Fat Distribution: A Systematic Review" Nutrients 2014, 6, 3895-3912 (Sep. 23, 2014).

Mohammed Gagaoua et al., "Decision tree, a learning tool for the prediction of beef tenderness using rearing factors and carcass characteristics" Journal of the Science of Food and Agriculture, vol. 99, Issue 3, Feb. 2019, pp. 1275-1283 (Aug. 3, 2018).

Loren M. Gianini et al., "Physical Activity and Post-Treatment Weight Trajectory in Anorexia Nervosa" Int J Eat Disord 2016; 49:482-489 (Dec. 29, 2015).

Wei Liu et al., "Long-Term Follow-up Study of MRI-Guided Bilateral Anterior Capsulotomy in Patients With Refractory Anorexia Nervosa" Neurosurgery Jul. 1, 2018;83(1):86-92. doi: 10.1093/neuros/nyx366.

Matteo Manuelli et a. "Body composition and resting energy expenditure in women with anorexia nervosa: Is hyperactivity a protecting factor?" Clin Nutr ESPEN Feb. 2019:29:160-164. doi: 10.1016/j.clnesp.2018.10.015. Epub Nov. 20, 2018.

Lori-An Etherington et al. "New Directions for Surgical Ablation Treatment of Obsessive Compulsive Disorder" Curr Top Behav Neurosci. 2021:49:437-460. doi: 10. 1007/7854_2020_207.

Chuan Shen et al., "Changes in ghrelin and obestatin levels before and after a meal in children with simple obesity and anorexia" Horm Res Paediatr. 2013;79(6):341-6. doi: 10.1159/000351464. Epub Jun. 13, 2013.

Terence Zimazile Sibanda et al. "Characterising Free-Range Layer Flocks Using Unsupervised Cluster Analysis" Animals (Basel). May 15, 2020;10(5):855. doi: 10.3390/ani10050855.

Ingrid Tonhajzerova et al., "Arterial stiffness and haemodynamic regulation in adolescent anorexia nervosa versus obesity" Appl Physiol Nutr Metab. Jan. 2020; 45(1):81-90. doi: 10.1139/apnm-2018-0867. Epub Jun. 4, 2019.

* cited by examiner

DTI Analysis

| Pre-MRgFUS | Post-MRgFUS |
|---|---|

| Number of Tracts | 1029 |
|---|---|
| Mean length | 64,0978 |

| Number of Tracts | 978 |
|---|---|
| Mean length | 57,9363 |

After 6 hours scanning MRgFUS

Follow-up : after 1 months MRgFUS

Follow-up : after 3 months MRgFUS

After MRgFus
6 hours

After MRgFus
1 months

After MRgFus
3 months

After MRgFus
6 months

METHODS OF TREATMENT FOR ANOREXIA NERVOSA

FIELD OF THE INVENTION

The field of the invention is treatments for anorexia nervosa. More particularly, the invention relates to methods for using a magnetic resonance guided focused ultrasound ("MRgFUS") treatment of anorexia nervosa.

BACKGROUND OF THE INVENTION

As a non-invasive and highly safe stereotactic treatment method, high-intensity focused ultrasound therapy has been approved by the Food and Drug Administrations of many countries for the treatment of essential tremor and Parkinson's disease. Drug-refractory psychiatric illness has a significant impact on society and is a great burden on families and patients. As a non-invasive treatment, magnetic resonance-guided focused ultrasound therapy has a wider application prospect in functional diseases and refractory psychiatric diseases.

Anorexia nervosa is a neuropsychiatric disorder that often occurs in young women. In the presence of severe mood disorders, patients will show extreme anorexia, dieting, and even abnormal vomiting behavior after overeating. Drug therapy is inadequate, and in severe cases, it can be life-threatening.

SUMMARY OF THE INVENTION

In this invention, a method is described for treating neurogenic anorexia nervosa in a subject in need thereof, using a magnetic resonance guided focused ultrasound treatment system. The method involves applying high-intensity focused ultrasound to multiple treatment target points on the bilateral anterior limbs of the left and right internal capsules of the subject's brain to regulate the bilateral anterior limbs, thereby aiding the subject in restoring normal weight. These multiple treatment target points are determined on-site during the MRgFUS treatment process using the MRgFUS treatment system.

In the human brain, the bilateral anterior limbs of the left and right internal capsules serve as crucial neural fiber bundle convergence pathways in the psychiatric circuitry, contributing positively to the regulation mechanism of treatment-resistant psychiatric disorders. The method described herein achieves the regulation of the bilateral anterior limbs of the internal capsules by applying high-intensity focused ultrasound (HIFU) energy to multiple treatment target points on the bilateral anterior limbs of the left and right internal capsules, i.e., by ablating these treatment target points for the purpose of regulating the bilateral anterior limbs; thereby helping to overcoming anorexic psychology or anorexic emotions associated with neurogenic anorexia nervosa. Additionally, since these treatment target points are determined on-site, it facilitates the formulation of more personalized treatment plans for the subjects by the physicians.

In some embodiments according to the present invention, each unilateral anterior limb is provided with at least four treatment target points. The method comprises applying high-intensity focused ultrasound energy to at least four treatment target points on each of the bilateral anterior limbs.

In some embodiments according to the present invention, each treatment target point is positioned using aRAS coordinate system in the MRgFUS treatment system; and the at least four treatment target points located on each of the bilateral anterior limbs are arranged from bottom to top in the SI direction in the RAS coordinate system. Specifically, the at least four treatment target points located on each of the bilateral anterior limbs have a total length measured along the SI direction of between 10 mm and 12 mm.

In some embodiments according to the present invention, adjacent target points of the at least four treatment target points located on each of the bilateral anterior limbs are spaced apart by 1-3 mm in the SI direction.

In some embodiments according to the present invention, adjacent two of the target points located on each of the bilateral anterior limbs are spaced apart by 2 mm in the SI direction.

In some embodiments according to the present invention, Among the at least four treatment target points on each of the bilateral anterior limbs, the treatment target point located at the lowest in the SI direction is 2 mm below the AC-PC plane.

In some embodiments according to the present invention, each treatment target point is located at the middle of the corresponding layer of the respective anterior limb in the T1WI axial slice image.

In some embodiments according to the present invention, applying high-intensity focused ultrasound energy to multiple treatment target points comprises applying energy to each treatment target point for achieving a maximum temperature of 47-63° C.

In some embodiments according to the present invention, applying high-intensity focused ultrasound energy to multiple treatment target points comprises applying the energy multiple times to each treatment target point.

In some embodiments according to the present invention, applying high-intensity focused ultrasound energy to multiple treatment target points comprises applying the energy to each treatment target point for no more than 3 times.

In some embodiments according to the present invention, applying the energy multiple times to each treatment target point comprises applying the energy with increasing intensity of the energy each time.

In some embodiments according to the present invention, applying the energy multiple times to each treatment target point comprises applying the energy with the same time each time.

In some embodiments according to the present invention, applying the energy multiple times to each treatment target point comprises applying energy for no more than 40 seconds at a time in succession.

In some embodiments according to the present invention, applying high-intensity focused ultrasound energy to multiple treatment target points comprises applying the energy of 10,000-30,000 joules at a time to each treatment target point.

In some embodiments according to the present invention, the method further comprises evaluating the effectiveness of treating anorexia nervosa, wherein evaluating the effectiveness of neurogenic anorexia nervosa treatment includes measuring MRI contrast before and after focused ultrasound treatment.

In some embodiments according to the present invention, the MRI contrast includes contrast in T1, T2, and SWI sequence scans.

In some embodiments according to the present invention, the magnetic resonance guided focused ultrasound (MRgFUS) treatment system includes: a magnetic resonance imaging (MRI) scanner configured to plan the therapy and monitoring the procedure in real-time; a high-intensity focused ultrasound (HIFU) transducer configured to deliver the ultrasound energy; a patient table configured to provide support for the subject during a treatment session, and the patient table being docked to the scanner; and a computer system operatively connected to the MRI scanner and the transducer.

In some embodiments according to the present invention, the magnetic resonance guided focused ultrasound (MRgFUS) treatment system also includes a cooling system for preventing overheating of the treated area and the ultrasound transducer.

In some embodiments according to the present invention, the transducer is designed as a helmet-like device equipped with multiple channel high-powered phased arrays for focusing the ultrasound energy.

DETAILED DESCRIPTION OF THE INVENTION

This application proposes a method for treating anorexia nervosa using MR-guided focused ultrasound (MRgFUS) therapy. Specifically, the method utilizes a MRgFUS (Magnetic Resonance guided Focused Ultrasound) treatment system to apply high-intensity focused ultrasound (HIFU) energy to multiple treatment target points on the anterior limbs of the bilateral internal capsules of the subject. This aims to implement a treatment approach that modulates a portion of the anterior limbs of the bilateral internal capsules through the applied energy to alleviate the symptoms of anorexia nervosa.

The MRgFUS treatment system is designed for treating neurological conditions without invasive surgery. It utilizes focused ultrasound energy to precisely target and ablate tissue deep within the brain, combining MRI technology with focused ultrasound to treat brain disorders.

Figure 1:
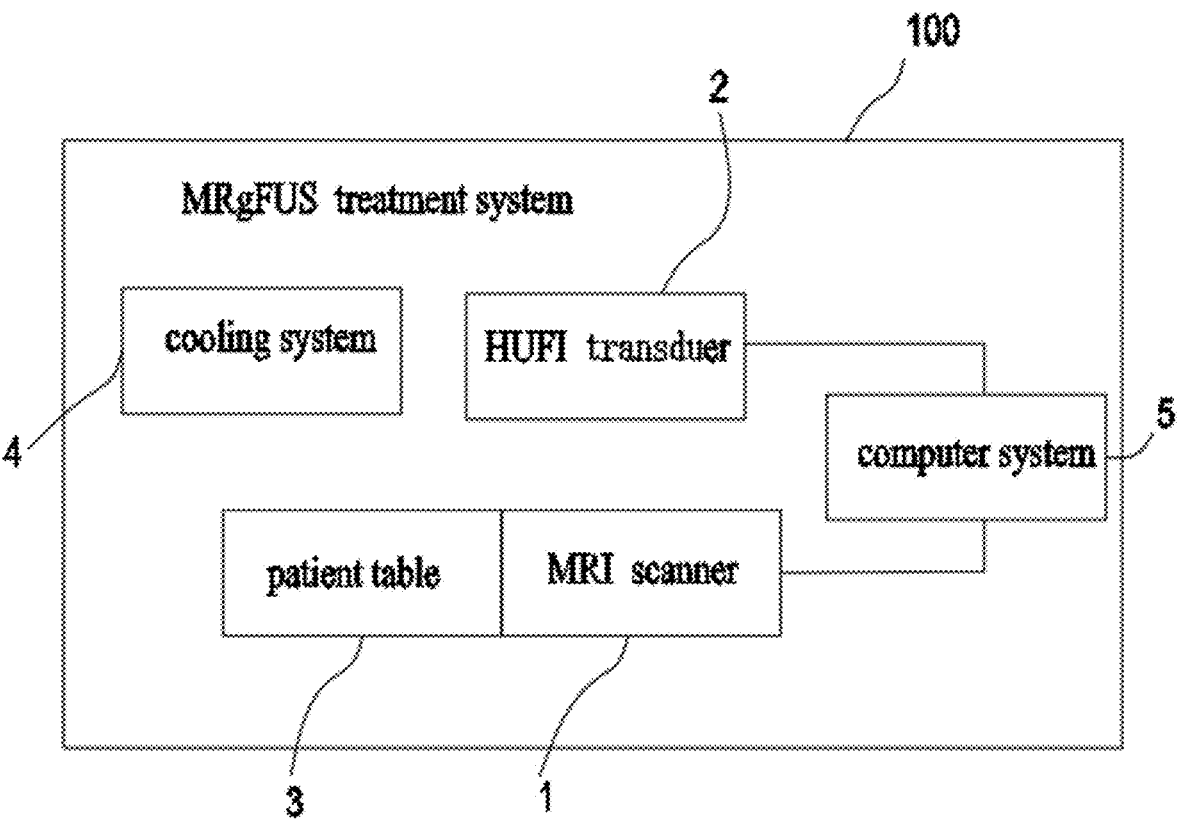
FIG. 1 illustrates a block diagram of the components of the MRgFUS treatment system.

Referring to FIG. 1, there is exemplified an MRgFUS treatment system 100. The system 100 consists mainly of components a MRI scanner 1, a high-intensity focused ultrasound (HIFU) transducer 2, a patient table 3, a cooling system 4 and a computer system 5.

The MRI scanner 1 is used for both planning the therapy and monitoring the procedure in real-time. This ensures that the targeted treatment area within the patient's brain is accurately visualized and treated.

The high-intensity focused ultrasound (HIFU) transducer 2 delivers the ultrasound energy. It is designed as a helmet-like device equipped with multiple channel high-powered phased arrays. These arrays focus ultrasound energy precisely on the targeted brain tissue to induce therapeutic effects without damaging surrounding tissues.

The patient table 3 is used for patients to lie down. The patient table is docked to the MRI scanner 1 and the integration allows for precise alignment and supports the patient comfortably during the treatment.

The cooling system 4 is configured to prevent overheating of the treated area and the ultrasound transducer 2. The cooling system helps maintain a constant temperature during the procedure, ensuring safety and comfort.

The computer system 5 is operatively connected to the MRI scanner land the HIFU transducer 2. The computer system 5 is backed by sophisticated software that processes the MRI data to guide the treatment. It includes algorithms for treatment planning, real-time monitoring, and adjustments to ensure the procedure is effective and safe.

In some embodiments of the MRgFUS system, in addition to the five components described above, the system includes components that enable remote control and monitoring capabilities. It can enhance flexibility in clinical settings and can facilitate collaboration among surgeons.

Figure 2:
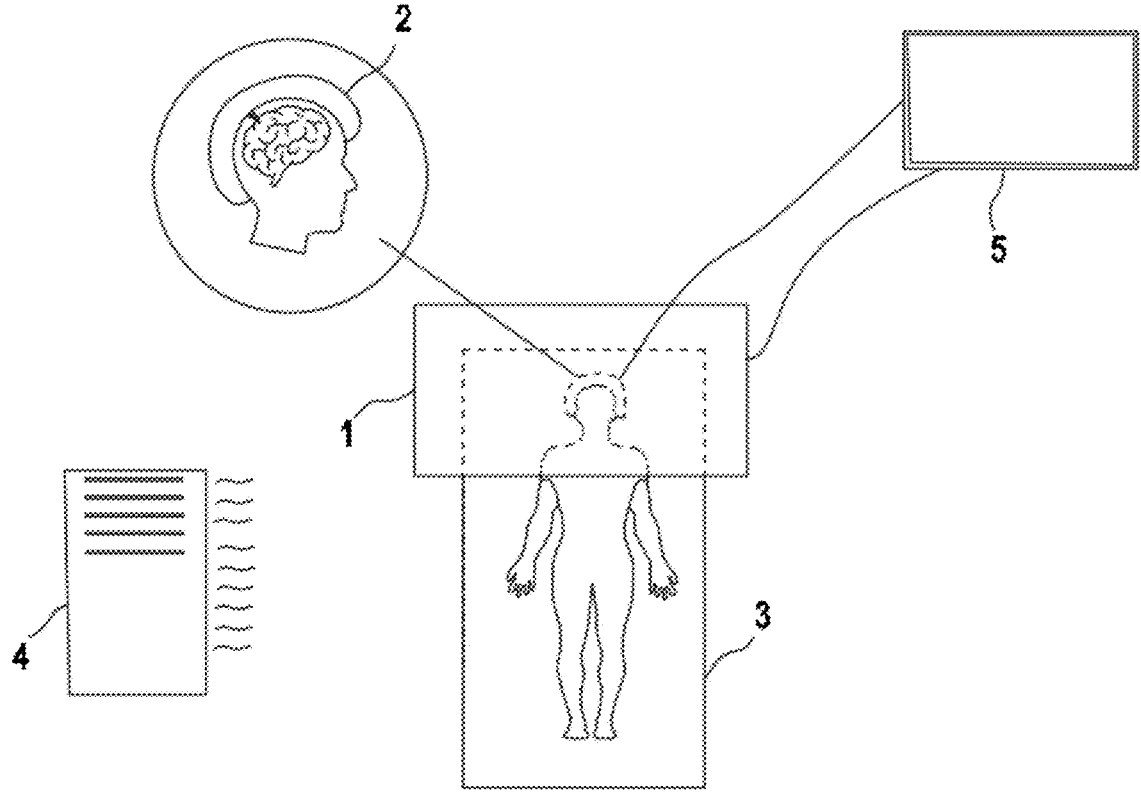
FIG. 2 illustrates the use of the MRgFUS treatment system for the subject with neurogenic anorexia nervosa.

Referring to FIG. 2, which illustrates a subject while utilizing the magnetic resonance guided focused ultrasound (MRgFUS) treatment system 100 for treating anorexia nervosa. During the surgical procedure, the subject lies on the patient table 3; the MRI scanner 1 can be used to acquire MRI image data of the subject's brain; the surgeon identifies the multiple treatment target points on-site with the help of the MRI image data on the computer system 5, and applies energy to the treatment target points using the HIFU transducer 2; and the cooling system maintains the constant temperature during the procedure.

Duet to limitations of existing hardware, the selection of multiple treatment target points needs to be more personalized. In this application, the multiple treatment target points are determined on-site during the treatment process using the MRgFUS treatment system. This on-site determination of treatment target points differs from the conventional approach of determining target points before surgery in traditional MRgFUS or other ablative surgeries.

In some applications described in this application, when determining multiple treatment target points, the anterior commissure/posterior commissure (AC/PC) points are first identified based on T1-weighted imaging scans to locate the anterior limbs of the left and right internal capsules. Then, multiple treatment target points in the bilateral anterior limbs of the left and right internal capsules are positioned.

The positioning method for the anterior limbs of the internal capsules can be described as follows: 10-12 mm anterior to the AC, 14-16 mm lateral to the midline, where the convergence of white fiber can be seen on the MRI structure.

The method of localization of multiple treatment target points can be described as follows: On the AC-PC plane, −2 mm is designated as the superior-inferior (SI) coordinate for the first treatment target point, and the medio-lateral (ML) coordinate for the first treatment target point is chosen as the middle position of the T1-weighted axial image of the anterior limb of the individual internal capsule at that level. After treating the first target point, the SI coordinate for the second target point is designated by moving 1-3 mm upward along the SI direction, and the ML coordinate for the second target point is chosen as the middle position of the T1-weighted axial image of the anterior limb of the respective internal capsule at that level. This process continues, moving upward along the SI direction, to designate subsequent treatment target points until all target points on one side of the anterior limb of the internal capsule are treated, followed by switching to multiple treatment target points on the other side.

In some embodiments, at least four target points are designated on each side of the anterior limb of the internal capsule, preferably four treatment target points.

In some embodiments, during the treatment of multiple treatment target points in the anterior limb of the respective internal capsule, the first treatment target point, the second treatment target point, etc., may not be treated in the order of the superior-inferior direction. For example, the first treatment target point may be treated first, followed by the second treatment target point, and then the treatment of the second treatment target point may be resumed. This situation may occur if the temperature rise at the second treatment target point meets the requirements in a short period, and temporary switching to the treatment of the next target point is needed.

Each treatment target point is localized using the RAS coordinate system in the MRgFUS treatment system. Multiple treatment target points on one side of the anterior limb of the internal capsule are arranged in the superior-inferior (SI) direction from bottom to top in the RAS coordinate system. Adjacent two treatment target points are preferably spaced 2 mm apart in the SI direction. In some embodiments, the total length measured along the SI direction for multiple treatment target points on one side of the anterior limb of the internal capsule is between 10 mm and 12 mm. This length measurement is from the bottom edge of the lowest treatment target point to the top edge of the highest treatment target point.

In this application, each treatment target point can undergo one or more applications of high-intensity focused ultrasound (HIFU), up to a maximum of 3 times, preferably 2 times. At each treatment target point, the intensity of the HIFU applied in multiple sessions may be incrementally increased, while the duration of each session of high-intensity focused ultrasound is preferably chosen to be the same. The intensity of high-intensity focused ultrasound applied in each session can be selected within the energy intensity range of 10,000-30,000 J/cm$^2$, and the duration of a single application should preferably not exceed 40 seconds. After completing the treatment at each treatment target point with high-intensity focused ultrasound, the highest temperature reached at each treatment target point should be between 47-60° C., such as 47° C., 53° C., 54° C., 57° C., 59° C., 60° C., 63° C., etc.

During the treatment of multiple treatment target points with high-intensity focused ultrasound energy, the treatment time for one or more treatment target points located at the front (in terms of the chronological order) is usually shorter, and the duration of a single session of high-intensity focused ultrasound is usually shorter. Conversely, the treatment time for multiple treatment target points located at the back is usually longer, and the duration of a single session of high-intensity focused ultrasound is usually longer. For example, using the treatment parameters of subject 1 as an example, where 10 treatment target points are designated in the bilateral anterior limbs of the internal capsule, the duration of a single session of high-intensity focused ultrasound applied to several treatment target points located at the front is chosen as 20 seconds, while the duration of a single session of high-intensity focused ultrasound applied to several treatment target points located at the back is chosen as 30 seconds. Additionally, several accuracy tests of high-intensity focused ultrasound application need to be conducted at the first treatment target point during the treatment process, where the temperature at this treatment target point is controlled to be below 50° C. during testing.

After completing high-intensity focused ultrasound treatment at all treatment target points, the purpose of modulating the bilateral anterior limbs of the subject's internal capsule can be achieved.

This method also includes evaluating the effectiveness of using the MRgFUS treatment system to treat anorexia nervosa. The effectiveness evaluation includes primary outcome measures such as changes in the subject's weight and BMI index, and secondary outcome measures such as changes in scores on psychological assessment scales like EAT-26, HAMA, HAMD, etc. For validated observation indicators, the MRI contrast (T1, T2, SWI sequence scans) before and after high-intensity focused ultrasound treatment is measured. In these scans, compared to the MRI signal before high-intensity focused ultrasound treatment, differential signals are observed in the treated target area after treatment (low signal on T1, high signal on T2, and iron deposition on SWI), indicating thermal coagulation effects of high-intensity focused ultrasound on brain structures and suggesting neuromodulation effects on actual neural fiber bundles.

Methods Used in Some Applications of the Present Invention

The following describes a series of protocols that can be selectively or collectively utilized based on the application of the present invention. It should be noted that the provided numerical values are illustrative rather than limiting. Similarly, while certain steps are described in detail, those skilled in the art will appreciate that other steps can be executed in a similar manner.

In accordance with some applications of the present invention, the following methods are employed:

Obtaining Subject and Control Population

According to the international clinical diagnostic criteria of DSM-5, patients meeting the diagnosis of anorexia nervosa are included. Informed consent is obtained through interviews with the subjects and their family members before implementing our MRI-guided focused ultrasound treatment.

This retrospective study has obtained ethical approval from the Ethics Committee of Shanghai International Medical Center (IRB-202311).

Assessment in Subject Criteria

Objective indicators include medical history, duration or disappearance of symptoms, changes in weight, and specialized symptom assessment scales for anorexia nervosa patients (such as EAT-26), used to determine the success rate and efficacy of treatment.

The study includes 4 patients with anorexia nervosa. All patients underwent follow-up assessments at 6 hours, 1 month, 3 months, and 6 months after treatment.

Imaging and Treatment

All subjects underwent MRgFUS bilateral anterior limb of the internal capsule focused ultrasound treatment using the ExAblate Neuro 4000 focused ultrasound system (Haifa, Insightec), targeting multiple treatment target points on both sides of the anterior limb of the internal capsule.

The positioning of the bilateral anterior limbs of the internal capsules was performed by locating the convergence of white fiber on the MRI structure, 10-12 mm anterior to the AC and 14-16 mm lateral to the midline. Subsequently, multiple treatment target points were determined on-site based on the condition of the subjects during the surgical procedure.

On the day of surgery, the subjects' hair was completely shaved. A stereotactic frame (CRW head frame) was fixed to the skull. The subject's head was then connected to the transducer base of the Insightec treatment bed. T2-weighted MRI scans were performed to re-evaluate the plan.

The MRgFUS treatment was performed using a 3-Tesla MRI (GE, Discovery 750w) and the ExAblate Neuro 4000 focused ultrasound system (Haifa, Insightec).

The treatment method involved applying high-intensity focused ultrasound (HIFU) energy from the high-intensity focused ultrasound source to each treatment target point location on the bilateral anterior limbs of the left and right internal capsules of the patient's brain. During the determination of each treatment target point, the SI coordinate for the first treatment target point was designated 2 mm below the AC-PC plane, and the ML coordinate was confirmed to be the middle position of the T1-weighted axial image of the anterior limb of the internal capsule at that level. After treating the first treatment target point 2-3 times (achieving a maximum temperature above 47° C.), the second treatment target point was designated by moving 1-3 mm upward along the SI direction, followed by the third and fourth treatment target points, all designated by moving upward 1-3 mm each time, resulting in 5-10 treatment target points on one side of the brain. During the surgical procedure, after confirming each treatment target point, energy was applied to that treatment target point; then, the next treatment target point was confirmed, and energy was applied at that treatment target point, until all treatment target points received energy application. During the surgical procedure, if the current treatment target point location cannot meet the temperature elevation requirements, other treatment target point locations can be switched to, and then return to the original treatment target point location for treatment.

During the application of high-intensity focused ultrasound energy, in addition to the initial accuracy testing phase (during which the ultrasound energy intensity increases from 3000 J to 5500 J), the specific parameters of applied energy levels ranging from 10,000 to 30,000 J (e.g., 13,000-27,000 J) will be determined by the temperature measured at the treatment target point. The target temperature is to achieve a maximum temperature of 47-60° C. at the corresponding treatment target point location.

Experimental Data

According to the techniques described in "Imaging and Treatment", 4 subjects underwent a MRgFUS surgical treatment, applying high-intensity focused ultrasound energy to multiple treatment target points on both left and right sides of the anterior limbs of the internal capsules.

The positions of all treatment target points determined during the treatment process for the 4 subjects are listed in Table 1 below; and the parameters of high-intensity focused ultrasound (HIFU) energy applied at each target point location for the 4 subjects are listed in Tables 2 to 5.

TABLE 1

| Target | Subject#1 | | | Subject#2 | | | Subject#3 | | | Subject#4 | | |
|---|---|---|---|---|---|---|---|---|---|---|---|---|
| NO. | ML | AP | SI | ML | AP | SI | ML | AP | SI | ML | AP | SI |
| 1 | 14.0 | 35.0 | 4.0 | 13.4 | 35.0 | −2.0 | 13.0 | 31.0 | 2.0 | 13.0 | 34.5 | −2.0 |
| 2 | 13.5 | 35.0 | 2.0 | 16.0 | 35.0 | 6.0 | 13.0 | 31.0 | 4.0 | 16.0 | 34.5 | 6.0 |
| 3 | 13.0 | 35.0 | 0.0 | 15.5 | 35.0 | 4.0 | 13.0 | 31.0 | 0.0 | 15.0 | 34.5 | 4.0 |
| 4 | 13.9 | 35.0 | −2.0 | 15.0 | 35.0 | 2.0 | 13.0 | 31.0 | −2.0 | 14.0 | 34.5 | 2.0 |
| 5 | 12.7 | 35.0 | −4.0 | 13.5 | 35.0 | 0.0 | 13.0 | 31.0 | −4.0 | 12.5 | 34.5 | 0.0 |
| 6 | −16.5 | 35.0 | 4.0 | −16.0 | 35.0 | 6.0 | −13.0 | 31.0 | 4.0 | −12.5 | 34.5 | −2.0 |
| 7 | −16.5 | 35.0 | 2.0 | −14.5 | 35.0 | 4.0 | −13.0 | 31.0 | 2.0 | −15.0 | 34.5 | 6.0 |
| 8 | −16.0 | 35.0 | 0.0 | −14.0 | 35.0 | 2.0 | −13.0 | 31.0 | 0.0 | −15.0 | 34.5 | 4.0 |
| 9 | −15.5 | 35.0 | −2.0 | −13.5 | 35.0 | 0.0 | −13.0 | 31.0 | −2.0 | −13.5 | 34.5 | 2.0 |
| 10 | −15.5 | 35.0 | −4.0 | −13.5 | 35.0 | −2.0 | −13.0 | 31.0 | −4.0 | −13.0 | 34.5 | 0.0 |

TABLE 2

| | | | | | | | Sonication Summary - subject #1 | | | | |
|---|---|---|---|---|---|---|---|---|---|---|---|
| Target | Sonication | | Parameters setting | | | | Actual power | Scan | Scan | Aver Temp | Max Temp |
| NO. | NO. | Time | Energy | Power | Time | | (J) | Dire | Freq | ° C. | ° C. |
| 1 | 1 (test) | 9:25 | 3000 | 300 | 15 | | 3002 | AX | AP | 43 | 44 |
| | 2 (test) | 9:28 | 3500 | 300 | 15 | | 3528 | AX | RL | 44 | 45 |
| | 3 (test) | 9:31 | 4000 | 350 | 15 | | 4024 | SA | AP | 43 | 44 |
| | 4 | 9:33 | 12050 | 798 | 20 | | 12099 | AX | AP | 53 | 58 |
| | 5 | 9:36 | 14050 | 847 | 20 | | 14081 | AX | AP | 53 | 57 |
| 2 | 6 | 9:45 | 13000 | 800 | 20 | | 13040 | AX | AP | 50 | 53 |
| | 7 | 9:52 | 15000 | 852 | 20 | | 13645 | AX | AP | 51 | 53 |
| 3 | 8 | 9:58 | 15000 | 900 | 20 | | 15055 | AX | AP | 52 | 55 |
| | 9 | 10:05 | 15000 | 900 | 20 | | 15044 | AX | AP | 51 | 53 |
| 4 | 10 | 10:14 | 19000 | 1003 | 20 | | 18100 | AX | AP | 54 | 57 |
| | 11 | 10:20 | 19500 | 1054 | 20 | | 18995 | AX | AP | 54 | 59 |
| 5 | 12 | 10:30 | 19000 | 1003 | 30 | | 19054 | AX | AP | 60 | 63 |

TABLE 2-continued

| | | | | Sonication Summary - subject #1 | | | | | | |
|---|---|---|---|---|---|---|---|---|---|---|
| Target | Sonication | | | Parameters setting | | | Actual power | Scan | Scan | Aver Temp | Max Temp |
| NO. | NO. | Time | Energy | Power | Time | (J) | Dire | Freq | ° C. | ° C. |
| 6 | 13 | 10:39 | 17000 | 900 | 20 | 16503 | AX | AP | 57 | 60 |
| | 14 | 10:45 | 19000 | 998 | 30 | 19001 | AX | AP | 57 | 60 |
| 7 | 15 | 10:51 | 17000 | 900 | 20 | 16623 | AX | AP | 51 | 53 |
| | 16 | 10:56 | 19000 | 998 | 30 | 19069 | AX | AP | 52 | 56 |
| 8 | 17 | 11:01 | 18000 | 900 | 30 | 18056 | AX | AP | 54 | 58 |
| | 18 | 11:06 | 19000 | 999 | 30 | 19047 | AX | AP | 54 | 58 |
| 9 | 19 | 11:12 | 18000 | 900 | 30 | 18079 | AX | AP | 53 | 55 |
| | 20 | 11:19 | 19000 | 999 | 30 | 19027 | AX | AP | 53 | 55 |
| 10 | 21 | 11:24 | 20000 | 997 | 30 | 20011 | AX | AP | 56 | 59 |
| | 22 | 11:28 | 21000 | 1045 | 30 | 21097 | AX | AP | 55 | 59 |

TABLE 3

| | | | | Sonication Summary - subject #2 | | | | | | |
|---|---|---|---|---|---|---|---|---|---|---|
| Target | Sonication | | | Parameters setting | | | Actual power | Scan | Scan | Aver Temp | Max Temp |
| NO. | NO. | Time | Energy | Power | Time | (J) | Dire | Freq | ° C. | ° C. |
| 2 | 1 (test) | 13:45 | 4000 | 400 | 15 | 4023 | AX | AP | 41 | 42 |
| | 2 (test) | 13:54 | 4500 | 400 | 15 | 4523 | AX | AP | 43 | 44 |
| | 3 | 14:00 | 14000 | 798 | 25 | 14034 | AX | AP | 49 | 52 |
| | 4 | 14:08 | 17500 | 900 | 30 | 17527 | AX | AP | 52 | 54 |
| 3 | 5 | 14:18 | 19000 | 950 | 30 | 19061 | AX | RL | 50 | 53 |
| | 6 | 14:24 | 21000 | 1000 | 30 | 21065 | SAG | AP | 50 | 54 |
| 4 | 7 | 14:34 | 23750 | 950 | 30 | 23757 | AX | RL | 52 | 55 |
| | 8 | 14:51 | 25050 | 1045 | 30 | 25119 | AX | RL | 51 | 55 |
| 5 | 9 | 15:04 | 25050 | 1050 | 30 | 25100 | AX | RL | 51 | 54 |
| | 10 | 15:17 | 26050 | 1050 | 30 | 26090 | AX | RL | 50 | 54 |
| 1 | 11 | 15:26 | 24000 | 1056 | 30 | 24042 | AX | RL | 46 | 49 |
| | 12 | 15:38 | 28000 | 1104 | 30 | 28105 | AX | RL | 48 | 50 |
| 6 | 13 | 15:44 | 24000 | 996 | 30 | 24058 | AX | RL | 53 | 55 |
| | 14 | 15:50 | 25000 | 996 | 30 | 25011 | AX | RL | 54 | 57 |
| 7 | 15 | 15:58 | 24000 | 996 | 30 | 24088 | AX | RL | 50 | 52 |
| | 16 | 16:00 | 26000 | 1092 | 30 | 26015 | AX | AP | 50 | 53 |
| 8 | 17 | 16:15 | 24000 | 996 | 30 | 24002 | AX | AP | 49 | 51 |
| | 18 | 16:18 | 26000 | 1092 | 30 | 26008 | AX | AP | 49 | 51 |
| 9 | 19 | 16:20 | 25000 | 996 | 30 | 25068 | AX | AP | 49 | 51 |
| | 20 | 16:25 | 26000 | 1092 | 30 | 26026 | AX | AP | 49 | 51 |
| 10 | 21 | 16:00 | 27000 | 1104 | 30 | 27008 | AX | AP | 51 | 52 |

TABLE 4

| | | | | Sonication Summary - subject #3 | | | | | | |
|---|---|---|---|---|---|---|---|---|---|---|
| Target | Sonication | | | Parameters setting | | | Actual power | Scan | Scan | Aver Temp | Max Temp |
| NO. | NO. | Time | Energy | Power | Time | (J) | Dire | Freq | ° C. | ° C. |
| 2 | 1 (test) | 9:26 | 3000 | 300 | 16 | 3002 | AX | AP | 42 | 43 |
| | 2 ( test) | 9:29 | 4000 | 400 | 20 | 4035 | AX | RL | 44 | 47 |
| | 3 (test) | 9:31 | 4500 | 400 | 20 | 4512 | SAG | AP | 44 | 46 |
| | 4 | 9:38 | 9500 | 903 | 25 | 9516 | AX | AP | 53 | 56 |
| | 5 | 9:43 | 10000 | 952 | 30 | 10049 | AX | RL | 53 | 57 |
| 3 | 6 | 9:55 | 11500 | 1002 | 30 | 11574 | AX | AP | 49 | 51 |
| | 7 | 10:01 | 14000 | 1002 | 30 | 14058 | AX | AP | 52 | 56 |

TABLE 4-continued

| | | | | | | | | | | |
|---|---|---|---|---|---|---|---|---|---|---|
| | | | | Sonication Summary - subject #3 | | | | | | |
| Target | Sonication | | Parameters setting | | | Actual power | Scan | Scan | Aver Temp | Max Temp |
| NO. | NO. | Time | Energy | Power | Time | (J) | Dire | Freq | ° C. | ° C. |
| 4 | 8 | 10:08 | 15000 | 1001 | 30 | 15080 | AX | AP | 54 | 58 |
| | 9 | 10:16 | 16500 | 1001 | 30 | 16522 | AX | RL | 54 | 59 |
| 1 | 10 | 10:27 | 16000 | 1001 | 30 | 16087 | AX | RL | 50 | 53 |
| | 11 | 10:34 | 19000 | 1099 | 30 | 19052 | AX | RL | 51 | 54 |
| 5 | 12 | 10:45 | 20000 | 1102 | 30 | 20052 | AX | AP | 51 | 54 |
| | 13 | 10:51 | 22000 | 1102 | 30 | 22058 | AX | AP | 50 | 54 |
| 6 | 14 | 10:58 | 22000 | 1000 | 30 | 1733 | AX | AP | 42 | 42 |
| | 15 | 11:00 | 22000 | 1000 | 30 | 16208 | AX | AP | 62 | 69 |
| 7 | 16 | 11:09 | 15000 | 997 | 30 | 15050 | AX | AP | 55 | 58 |
| 8 | 17 | 11:15 | 14024 | 1001 | 30 | 14024 | AX | RL | 54 | 58 |
| 9 | 18 | 11:22 | 16000 | 1099 | 30 | 16100 | AX | RL | 53 | 56 |
| | 19 | 11:27 | 18000 | 1145 | 30 | 18061 | AX | AP | 55 | 60 |
| 10 | 20 | 11:31 | 16000 | 1104 | 30 | 16005 | AX | AP | 53 | 57 |
| | 21 | 11:37 | 20000 | 1149 | 30 | 20027 | AX | AP | 52 | 55 |

TABLE 5

| | | | | | | | | | | |
|---|---|---|---|---|---|---|---|---|---|---|
| | | | | Sonication Summary - subject #4 | | | | | | |
| Target | Sonication | | Parameters setting | | | Actual power | Scan | Scan | Aver Temp | Max Temp |
| NO. | NO. | Time | Energy | Power | Time | (J) | Dire | Freq | ° C. | ° C. |
| 1 | 1 (test) | 9:40 | 4500 | 450 | 20 | 4509 | AX | AP | 42 | 43 |
| | 2 (test) | 9:45 | 5000 | 450 | 20 | 5013 | AX | RL | 42 | 43 |
| | 3 (test) | 9:48 | 5500 | 450 | 20 | 5524 | SAG | AP | 41 | 43 |
| | 4 | 9:56 | 18000 | 999 | 25 | 18082 | AX | AP | 50 | 53 |
| | 5 | 10:02 | 24000 | 999 | 25 | 22678 | AX | AP | 51 | 54 |
| 2 | 6 | 10:16 | 23750 | 1055 | 25 | 23797 | AX | RL | 51 | 54 |
| | 7 | 10:18 | 25150 | 1030 | 25 | 21678 | AX | AP | 53 | 49 |
| 3 | 8 | 10:30 | 26250 | 1103 | 30 | 26317 | AX | RL | 50 | 52 |
| | 9 | 10:37 | 28050 | 1155 | 30 | 28123 | AX | RL | 49 | 53 |
| 4 | 10 | 10:47 | 30000 | 1104 | 30 | 30051 | AX | AP | 52 | 55 |
| | 11 | 11:00 | 31000 | 1104 | 30 | 28107 | AX | AP | 50 | 54 |
| 5 | 12 | 11:07 | 30000 | 1152 | 30 | 30072 | AX | AP | 51 | 54 |
| | 13 | 11:13 | 31000 | 1152 | 30 | 31024 | AX | AP | 50 | 52 |
| 6 | 14 | 11:26 | 30000 | 1152 | 30 | 30028 | AX | AP | 55 | 58 |
| | 15 | 11:33 | 31000 | 1152 | 30 | 30795 | AX | AP | 53 | 56 |
| 7 | 16 | 11:38 | 30000 | 1152 | 30 | 28550 | AX | AP | 52 | 54 |
| | 17 | 11:52 | 31000 | 1152 | 30 | 30664 | AX | AP | 51 | 54 |
| 8 | 18 | 11:56 | 30000 | 1152 | 30 | 28491 | AX | AP | 50 | 53 |
| | 19 | 12:04 | 31000 | 1152 | 30 | 30985 | AX | AP | 50 | 52 |
| 9 | 20 | 12:14 | 30000 | 1152 | 30 | 30037 | AX | AP | 51 | 54 |
| | 21 | 12:21 | 31000 | 1152 | 30 | 31103 | AX | AP | 50 | 51 |
| 10 | 22 | 12:30 | 30000 | 1200 | 20 | 30093 | AX | AP | 50 | 51 |
| | 23 | 12:45 | 32000 | 1200 | 20 | 32005 | AX | RL | 52 | 52 |

All subjects underwent preoperative MRI examinations. All MRI studies were conducted using a 3 Tesla system (GE, 750w, DV26). After treatment, all subjects underwent post-operative MRI examinations at 6 hours, 1 month, 3 months, and 6 months. MRI examinations revealed abnormal signals in the tail nucleus and anterior limb of the internal capsule in all subjects after surgery, which were considered to be the effects of ultrasound modulation. This suggests a thermal coagulation effect of focused ultrasound on brain structures and indicates neuromodulation effects on actual neural fiber bundles.

As an example, the diffusion tensor imaging (DTI) images of the anterior limbs of the internal capsules' neural fiber bundles for subject 1 #before surgery and 6 hours after surgery, as well as the postoperative MRI examinations of subject 1 #at 6 hours, 1 month, 3 months, and 6 months, are provided below.

Figure 3:
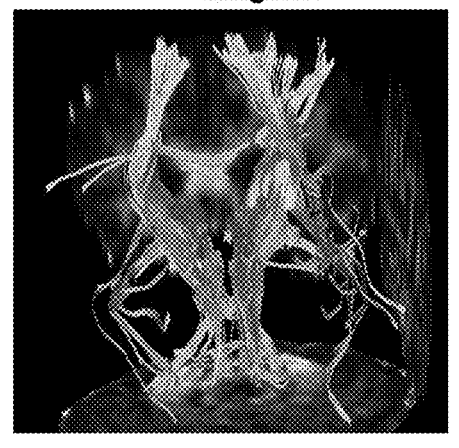
FIG. 3 shows the comparison of the diffusion tensor imaging (DTI) results of the neural fiber bundle in the anterior limbs of the internal capsules of subject 1 before and after surgery.
Figure 3:
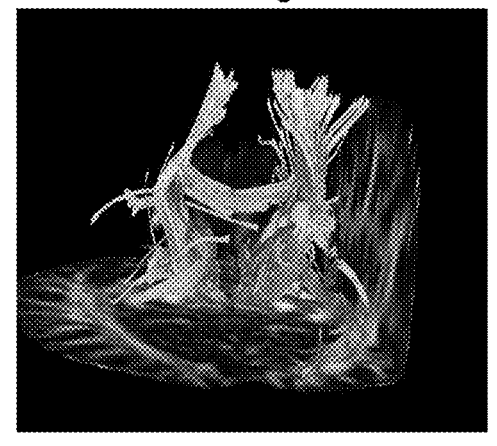

Referring to FIG. 3, the number of nerve fiber bundles in the anterior limbs area of the internal capsules of subject 1 #was significantly reduced, suggesting that the modulation of the ultrasound beams may have an effect on the connection of the nerve fiber bundles, which may have an inhibitory effect on the excitatory neural circuits or an excitatory effect on the inhibited ones, and the specific mechanism needs to be further investigated. However, from the results of DTI analysis, it is possible to show that there is a direct effect on the neural connections in the brain.

Figure 4:
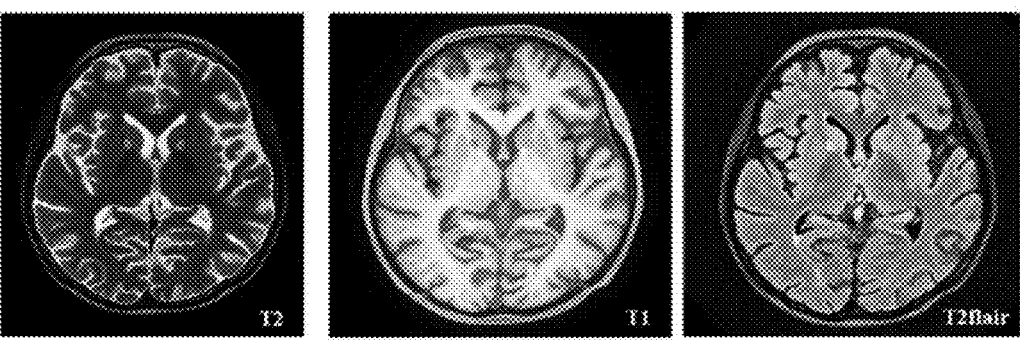
FIG. 4 shows the comparison of axial MRI images of subject 1 taken at 6 hours, 1 month, 3 months, and 6 months post-operation.
Figure 4:
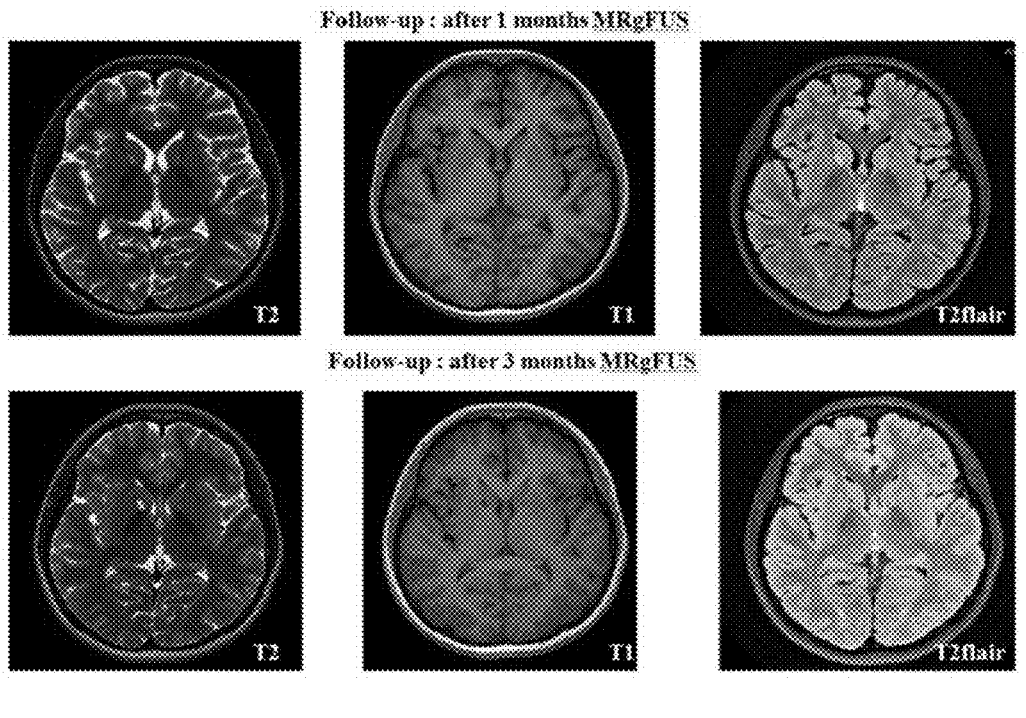
Figure 4:
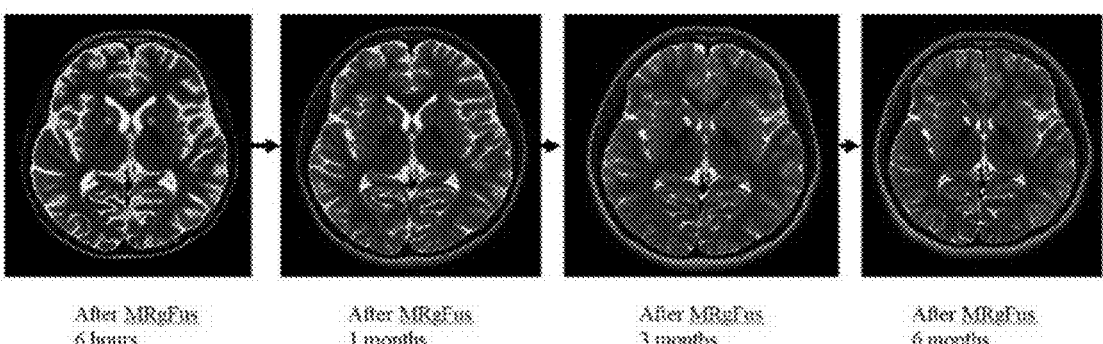

Referring to FIG. 4, Subject 1 #was seen to have visible signal changes in the region of the anterior limbs of the internal capsules and the caudate nuclei bilaterally on MRI structural image scans before and after treatment, and this abnormal signal persisted during follow-up, indirectly corroborating the structural changes of our treatment.

Without being bound by theory, it is believed the crucial neural fiber bundle convergence pathways at the bilateral anterior limbs of the left and right internal capsules of the subject 1 #have been reconstructed after applying the HIFU energy to the treatment target points.

The weight parameters of the 4 subjects after postoperative recovery are shown in Table 6.

TABLE 6

| Subject No. | age | gender | Follow-up | Weight (before) | Weight (after) | BMI (before) | BMI (after) | Accompany | Adverse event |
|---|---|---|---|---|---|---|---|---|---|
| 1# | 15 | F | 12 | 23 kg | 41 | 8.19 | 13.2 | none | / |
| 2# | 18 | F | 12 | 27 kg | 40 | 10.2 | 15.3 | none | / |
| 3# | 20 | F | 10 | 32 kg | 45 kg | 11.2 | 16.3 | vomiting | / |
| 4# | 19 | F | 6 | 35 | 42 | 10.8 | 14.5 | none | / |

From the data presented in Table 6, it can be observed that the weight of all 4 subjects significantly increased after surgery, indicating that the MRgFUS surgery has a positive effect on treating anorexia nervosa.

It will be appreciated that additional advantages and modifications will readily occur to those skilled in the art. Therefore, the disclosures presented herein and broader aspects thereof are not limited to the specific details and representative embodiments shown and described herein. Accordingly, many modifications, equivalents, and improvements may be included without departing from the spirit or scope of the general inventive concept as defined by the appended claims and their equivalents.

The invention claimed is:

1. A method for treating neurogenic anorexia nervosa in a subject in need thereof, using a magnetic resonance guided focused ultrasound (MRgFUS) treatment system, the method comprising:

applying high-intensity focused ultrasound (HIFU) energy to multiple treatment target points on bilateral anterior limbs of the left and right internal capsules of the subject in a MRgFUS treatment to regulate the bilateral anterior limbs, wherein the multiple treatment target points are determined on-site during the MRgFUS treatment; and inducing normalization of weight in the subject, wherein applying high-intensity focused ultrasound energy to multiple treatment target points on bilateral anterior limbs comprises applying high-intensity focused ultrasound energy to at least four treatment target points on each of the bilateral anterior limbs; and wherein each treatment target point is positioned using a right anterior superior (RAS) coordinate system in the MRgFUS treatment system; and the at least four treatment target points located on each of the bilateral anterior limbs are arranged from bottom to top in the SI direction in the RAS coordinate system.

2. The method according to claim 1, wherein the at least four treatment target points located on each of the bilateral anterior limbs have a total length measured along the SI direction of between 10 mm and 12 mm.

3. The method according to claim 1, wherein adjacent treatment target points of the at least four treatment target points located on each of the bilateral anterior limbs are spaced apart by 1-3 mm in the SI direction.

4. The method according to claim 3, wherein adjacent treatment target points of the at least four treatment target points located on each of the bilateral anterior limbs are spaced apart by 2 mm in the SI direction.

5. The method according to claim 1, wherein among the at least four treatment target points on each of the bilateral anterior limbs, the treatment target point located at the lowest in the SI direction is 2 mm below the AC-PC plane.

6. The method according to claim 1, wherein each treatment target point is located in the middle of the corresponding layer of the respective anterior limb in the T1WI axial slice image.

7. The method according to claim 1, wherein applying high-intensity focused ultrasound energy to multiple treatment target points comprises applying energy to each of the multiple treatment target points for achieving a maximum temperature of 47-63° C.

8. The method according to claim 1, wherein applying high-intensity focused ultrasound energy to multiple treatment target points comprises applying the energy multiple times to each treatment target point.

9. The method according to claim 8, wherein applying high-intensity focused ultrasound energy to multiple treatment target points comprises applying the energy to each treatment target point for no more than 3 times.

10. The method according to claim 8, wherein applying the energy multiple times to each treatment target point comprises applying the energy with increasing intensity of the energy each time.

11. The method according to claim 8, wherein applying the energy multiple times to each treatment target point comprises applying the energy with the same time each time.

12. The method according to claim 8, wherein applying the energy multiple times to each treatment target point comprises applying the energy for no more than 40 seconds at a time in succession.

13. The method according to claim 1, wherein applying high-intensity focused ultrasound energy to multiple treatment target points comprises applying the energy of 10,000-30,000 joules at a time to each treatment target point.

14. The method according to claim 1, further comprising: evaluating the effectiveness of neurogenic anorexia nervosa treatment; wherein evaluating the effectiveness of neurogenic anorexia nervosa treatment includes measuring the MRI contrast of the subject before and after the MRgFUS treatment.

15. The method according to claim 14, wherein the MRI contrast includes T1, T2, and SWI sequence scan imaging manifestations contrast.

16. The method according to claim 1, wherein the magnetic resonance guided focused ultrasound (MRgFUS) treatment system includes:

a magnetic resonance imaging (MRI) scanner configured to plan the therapy and monitoring the procedure in real-time;

a high-intensity focused ultrasound (HIFU) transducer configured to deliver the ultrasound energy;

a patient table configured to provide support for the subject during a treatment session, and the patient table being docked to the scanner; and a computer system operatively connected to the MRI scanner and the transducer.

17. The method according to claim 16, wherein the magnetic resonance guided focused ultrasound (MRgFUS) treatment system also includes a cooling system for preventing overheating of the treated area and the ultrasound transducer.

18. The method according to claim 16, wherein the transducer is designed as a helmet-like device equipped with multiple channel high-powered phased arrays for focusing the ultrasound energy.

\* \* \* \* \*